(12) United States Patent
Soltanpour et al.

(10) Patent No.: US 6,682,500 B2
(45) Date of Patent: Jan. 27, 2004

(54) SYNTHETIC MUSCLE BASED DIAPHRAGM PUMP APPARATUSES

(76) Inventors: David Soltanpour, 5 Lindsley Dr., Larchmont, NY (US) 10538; Mohsen Shahinpoor, 9910 Tanoan Dr. NE., Albuqerque, NM (US) 87111

( * ) Notice: Subject to any disclaimer, the term of this patent is extended or adjusted under 35 U.S.C. 154(b) by 0 days.

(21) Appl. No.: 09/841,191

(22) Filed: Apr. 25, 2001

(65) Prior Publication Data

US 2002/0013545 A1 Jan. 31, 2002

Related U.S. Application Data

(63) Continuation-in-part of application No. 09/586,962, filed on Jun. 5, 2000, which is a continuation-in-part of application No. 09/015,759, filed on Jan. 29, 1998, now Pat. No. 6,168,575.

(51) Int. Cl.[7] .................... A61M 5/00; A61M 31/00; A61K 9/22
(52) U.S. Cl. .................... 604/9; 604/521; 604/891.1
(58) Field of Search ................ 604/8, 9, 149, 604/151, 123, 119, 521, 131–133, 890.1, 891.1; 623/14.13, 3.12, 6.14, 23.68; 210/436, 472

(56) References Cited

U.S. PATENT DOCUMENTS

| | | | | |
|---|---|---|---|---|
| 5,062,841 A | * | 11/1991 | Siegel | 424/423 |
| 5,171,775 A | * | 12/1992 | Graiver et al. | 524/503 |
| 5,389,222 A | * | 2/1995 | Shahinpoor | 204/607 |
| 6,203,291 B1 | * | 3/2001 | Stemme et al. | 137/833 |

\* cited by examiner

Primary Examiner—Angela D. Sykes
Assistant Examiner—Leslie Deak
(74) Attorney, Agent, or Firm—Alfred F. Hoyte, Jr.

(57) ABSTRACT

Implantable, pressure adjustable diaphragm pump systems which are scalable and are characterized by a common type of actuating mechanism. The pumps may be inductively and transcutaneously powered via adjacent, mutually inductive electromagnetic coils. Alternatively the pumps may be effectively "self" powered using a synthetic muscle attached to a local bending or twisting force. The pumps may be used in a range of applications from mechanical applications to medical applications such as intraocular pressure control for glaucoma patients, bodily fluid drainage control, and drug delivery systems. These pump systems each include a pumping chamber having an anterior end attached to an implantable influent conduit. In the case of an ocular pressure control device, the influent conduit is inserted into the anterior chamber of the eye. A flexing ionic polymer conductor composite IPCC synthetic muscle, which is a type of ionic polymer metal composite (IPMC) synthetic muscle, functions as the primary actuator. The posterior end of the pumping chamber is connected to an effluent or drainage conduit, which may drain bodily fluids or dispense drugs to an area of the body. A key feature of the invention is the self or secondary power generation system in the form of a much larger piece of IPCC synthetic muscle which, in the case of glaucoma prevention systems, may be placed on the globe surface (sclera) of the eye and attached to and secured by the extraocular muscles of the eye. An alternative external power system includes a biocompatible induction coil with gold wire armature that can be transcutaneously activated, adjusted, and computer-interrogated and controlled by a surgeon. The device of the invention is further equipped with a pair of adjustable variable flow valves placed at the juncture of the inlet and effluent conduits with the pumping chamber. The valves are used to regulate fluid flow through the pumping chamber. A pressure regulating system including a pressure sensor and pump controlling microprocessor may also be used with the inventive system.

10 Claims, 3 Drawing Sheets

SYNTHETIC MUSCLE BASED DIAPHRAGM PUMP APPARATUSES

CROSS REFERENCE TO RELATED APPLICATIONS

This application is a continuation in part of application Ser. No. 09/586,962, filed on Jun. 5, 2000, which is a continuation in part of application Ser. No. 09/015,759, filed on Jan. 29, 1998.

BACKGROUND OF THE INVENTION

1. Field of the Invention

The present invention relates to pump assemblies. More specifically, it relates to improved diaphragm pumps in a range of sizes, including micro-miniature pumps which may be used as bio-compatible medical implants for controlling diseases such as glaucoma and for controlled delivery of drugs.

2. Description of the Prior Art

Mechanical and electromechanical medical implants are well known and, depending upon the type, have met with varying success rates. One problem with these devices is the lack of a reliable, long term power source. Ideally, the power source should last for the life of the implant, as many of these implants require invasive procedures both to install and maintain. Indeed, an external power source is virtually impossible in many situations.

One use for mechanical implants is the treatment of glaucoma. Glaucoma is a common eye disease which is caused by excessive ocular pressure in the anterior chamber of the eyeball. Many devices and techniques have been devised in order to control this pressure. The devices fall generally into two types; passive devices such as a simple tubular shunt or similar device which drains aqueous humor from the anterior chamber, and active devices which have means for controllably draining ocular pressure, the systems typically using check valves or similar mechanical devices. While these systems are somewhat effective, they all tend to suffer from the drawback in that they are unreliable or require frequent maintenance which always involves a fairly invasive procedure. Failure to properly maintain the devices can result in long term damage to the eye.

Recently, mechanical devices have been used in order to effect controlled delivery of drugs. These devices are almost all passive, with the exception of a few highly experimental devices such as nanobots. Mechanical devices, while possessing many advantages, are rarely used as the reliability of passive devices is already established, albeit with the aforementioned shortcomings.

U.S. Pat. No. 5,370,607 issued to Memmen discloses a glaucoma implant device which has a tubular shunt for draining fluid from the eye. By contrast, the present invention contemplates a controllable, self or inductively powered pumping mechanism for draining fluid from the eye to treat glaucoma.

U.S. Pat. No. 4,911,616 issued to Laumann, Jr. discloses a microminiature pump which may be used to administer medications in sensitive locations in the body such as the eye. The pump is programmable, but the patent does not disclose which aspects of the pump operation can be controlled. Also, the pump requires a separate power source. By contrast, the present invention contemplates a miniature pump and conduit assembly which may be used, among other things, to control glaucoma by controllably pumping fluid from the eye in accordance with sensed pressure conditions within the eye.

U.S. Pat. No. 5,062,841 issued to Siegel discloses an insulin pump which can be used to pump insulin directly into the bloodstream in response to blood glucose levels. By contrast, the present invention contemplates an inductively powered miniature pump which can be implanted into the tissue surrounding the eye and can controllably reduce ocular pressure.

U.S. Pat. No. 5,433,701 issued to Rubinstein discusses an active ocular pressure control device which includes a pump which is selectively operated in response to a control signal from a pressure sensor. However, no details as to the power source or structure of the pump, microprocessor, or pressure sensing means are disclosed.

The present invention contemplates a diaphragm pumping system, the size of the pump determined by the intended use. Prior art diaphragm pumps generally are relatively large and are characterized by a pumping chamber, in fluid communication with influent and effluent conduits, with a mechanical driver serving to force fluid into and through the inlet. Fluid is forced out of the effluent conduit by the driver, typically a piston, which is invariably positioned in a substantially central main body or housing. Contained within the housing is the pumping chamber, as well as a chamber containing hydraulic fluid called the transfer chamber. The transfer chamber and the pumping chamber are separated by a flexible diaphragm. Reciprocal movement of the piston causes flexing of the diaphragm which effects fluid movement through the pumping chamber. The influent and effluent conduits may both have check valves for limiting fluid flow through the pumping chamber.

SUMMARY OF THE INVENTION

The present invention concerns implantable, pressure adjustable diaphragm pump systems which are scalable and are characterized by a common type of actuating mechanism. The pumps may be inductively and transcutaneously powered via adjacent, mutually inductive electromagnetic coils. Alternatively the pumps may be effectively "self" powered using a synthetic muscle attached to a local bending or twisting force. The pumps may be used in a range of applications from mechanical applications to medical applications such as intraocular pressure control for glaucoma patients, bodily fluid drainage control, and drug delivery systems. These pump systems each include a pumping chamber having an anterior end attached to an implantable influent conduit. In the case of an ocular pressure control device, the influent conduit is inserted into the anterior chamber of the eye. A flexing ionic polymer conductor composite IPCC synthetic muscle, which is a type of ionic polymer metal composite (IPMC) synthetic muscle, functions as the primary actuator. The posterior end of the pumping chamber is connected to an effluent or drainage conduit, which may drain bodily fluids or dispense drugs to an area of the body. A key feature of the invention is the self or secondary power generation system in the form of a much larger piece of IPCC synthetic muscle which, in the case of glaucoma prevention systems, may be placed on the globe surface (sclera) of the eye and attached to and secured by the extraocular muscles of the eye. An alternative external power system includes a biocompatible induction coil with gold wire armature that can be transcutanously activated, adjusted, and computer-interrogated and controlled by a surgeon. The device of the invention is further equipped with a pair of adjustable variable flow valves placed at the juncture of the inlet and effluent conduits with the pumping chamber. The valves are used to regulate fluid flow through the pumping chamber. A pressure regulating system including a pressure sensor and pump controlling microprocessor may also be used with the inventive system.

The pumping system employs ionic polymer metal composite (IPMC) synthetic muscles. These synthetic muscles are made from ionic polymeric (polyelectrolyte) gels chemically treated with platinum (IPPC). They exhibit large motion sensing and actuation capabilities in a distributed manner. IPMCs are three-dimensional networks of cross-linked macromolecular polyelectrolytes with internal electrodes that swell, shrink, bend or generally deform in an electric field. Conversely, IPMCs are capable of generating an electric field or voltage as a result of being manipulated. Thus, direct computer control and monitoring of large expansions and contractions of ionic polymeric gel-noble metal composite muscles by means of a voltage controller has been achieved. The IPMCs require only a few volts for actuation. These muscles can be cut as small as needed and still preserve their functional properties. Accordingly, this technology is incorporated into the present invention as will be explained in more detail later.

Accordingly, it is a principal object of the invention to provide a self powered diaphragm pump having a synthetic muscle actuator.

It is a major object of this invention to provide a family of implantable pump assemblies having a common actuator mechanism, the size and shape of the pump and the actuator mechanism selected in accordance with a predetermined function.

It is another object of this invention to provide a family of implantable pump assemblies having a common actuator mechanism, the size and shape of the pump housing selected in accordance with the physical parameters of an intended implant area.

It is another object of the invention to provide such a pump assembly having an automatically controlled pumping rate.

It is still another object of the invention to provide an improved, biologically implantable pump assembly having a pumping rate which is controllable in response to sensed local pressure conditions.

It is another object of the invention to provide an implantable pump assembly which can derive electrical power from muscle movement.

It is another object of the invention to provide an implantable pump assembly which can be used to administer drugs.

It is another object of the invention to provide a miniature pumping system for controlling ocular pressure having means to generate power from the movement of the ocular muscle.

It is another object of the invention to provide a miniature pumping system which can be interrogated electronically while remaining implanted in the body.

It is another object of the invention to provide an improved method and apparatus for controlling glaucoma including a micropump which is implanted into the anterior chamber of the eye.

It is another object of the invention to provide an improved method and apparatus for controlling glaucoma including a micropump where pump operation is controlled in accordance with the disease state of the optic nerve and the sensed ocular pressure.

It is yet another object of the invention to provide an improved, biologically implantable pump assembly having a draining tube with a relatively wide outlet end to disperse the outflow of fluid.

It is yet another object of the invention to provide an improved, biologically implantable synthetic muscle based diaphragm pump assembly having constant flow therethrough to prevent occlusion of the drainage tube.

Finally, it is a general object of the invention to provide improved elements and arrangements thereof in an apparatus for the purposes described which is dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1A:
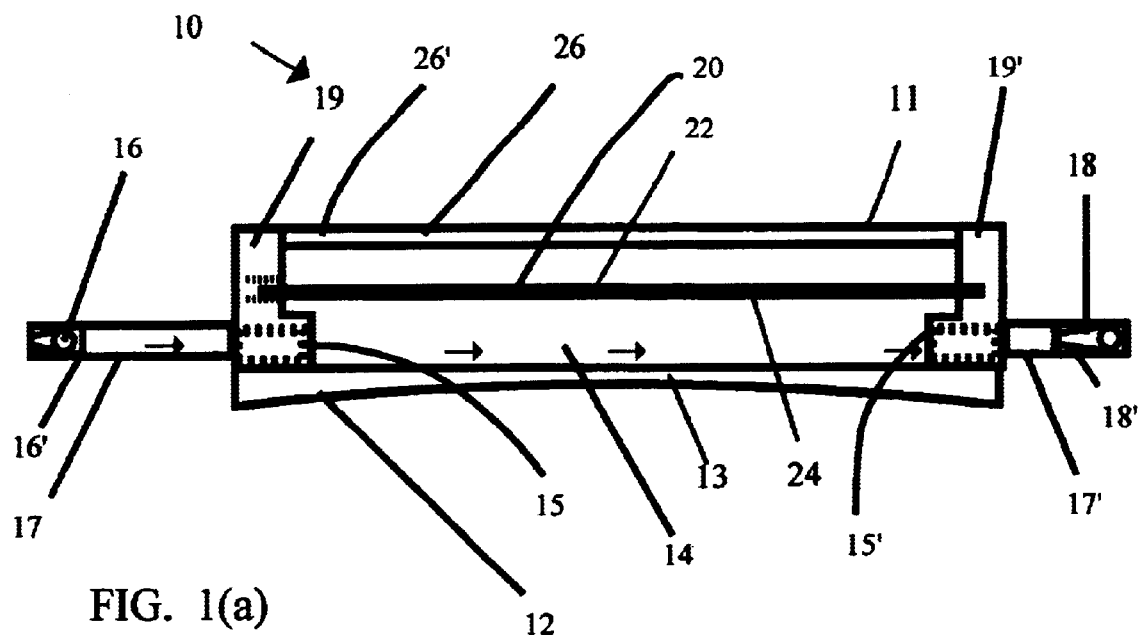
FIG. 1(a) is a side elevational view, partly in section, of the basic structure of a pump assembly of the present invention.

Referring now to FIGS. 1(a)–4, a pump assembly, generally indicated by the numeral 10, is shown. The assembly 10 is of a sufficient size to perform its intended function but the structure is essentially the same regardless of size. Thus, if the assembly 10 is used as an ocular implant to treat glaucoma it would be relatively small, whereas a mechanical application (e.g., as a machine component) would require a much larger pump assembly 10. The primary actuator of the assembly 10 is the diaphragm 20 shown in the rest (non-deflected) position in FIG. 1. In accordance with a preferred embodiment of the invention, the diaphragm 20 is made from an ionic polymeric synthetic muscle material. U.S. Pat. Nos. 5,389,222, issued to Shahinpoor and 6,109,852 issued to Shahinpoor, et al. both disclose exemplary synthetic muscle materials from which diaphragm 20 may be made and are herein incorporated by reference. The synthetic muscle materials disclosed by Shahinpoor can be flexed by the application of an electrical voltage thereto. The amount and direction of the flexure is primarily a function of the magnitude and polarity of the applied voltage, respectively. In the embodiments shown the assembly 10 includes a housing 11 which is substantially flat, but in accordance with one aspect of the invention the outer surface 12 of the bottom panel 13 may be contoured in accordance with the physical parameters of an implant area, if the pump 10 is to be used as a bio-implant, or contoured in accordance with the environment in which the pump 10 is used. Thus, for example, if the assembly 10 is used to treat glaucoma, outer surface 12 may be substantially curved to approximate the curvature of the eyeball. The assembly 10 includes a pumping chamber 14, defined by mutually opposed end panels 19, 19', side panels 21, 21', and a cover or top panel 26. Openings 15, 15' formed in mutually opposed end panels 19, 19' allow for fluid flow into and through an inlet conduit 17 which is affixed within opening 15 in fluid tight relation thereto, into the pumping chamber 14, and out through outlet conduit 17' which is secured in fluid tight relation within opening 15'. A one way check valve 16 and associated stop partition 16' serve to selectively permit fluid flow into the conduit 17 as will be explained in more detail later. Outlet conduit 17' includes check valve 18 and associated stop partition 18' which serves to selectively permit fluid flow from the pumping chamber 14.

Figure 1B:
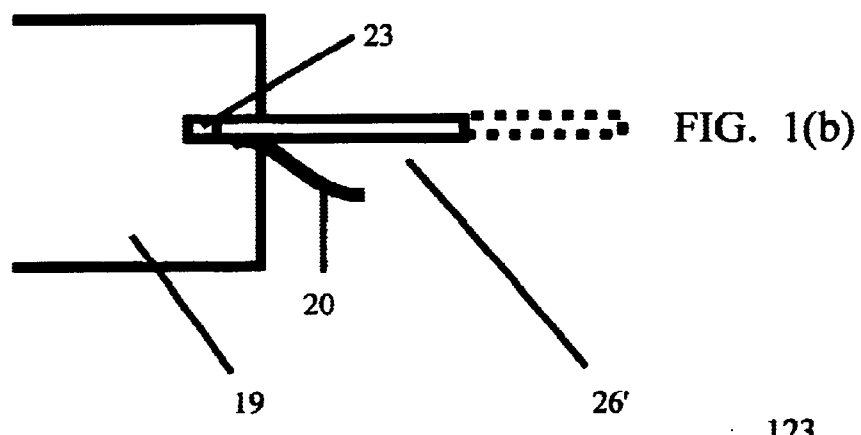
FIG. 1(b) is a sectional view of a detail of FIG. 1(a) detailing the attachment of the diaphragm within the pump housing.
Figure 1C:
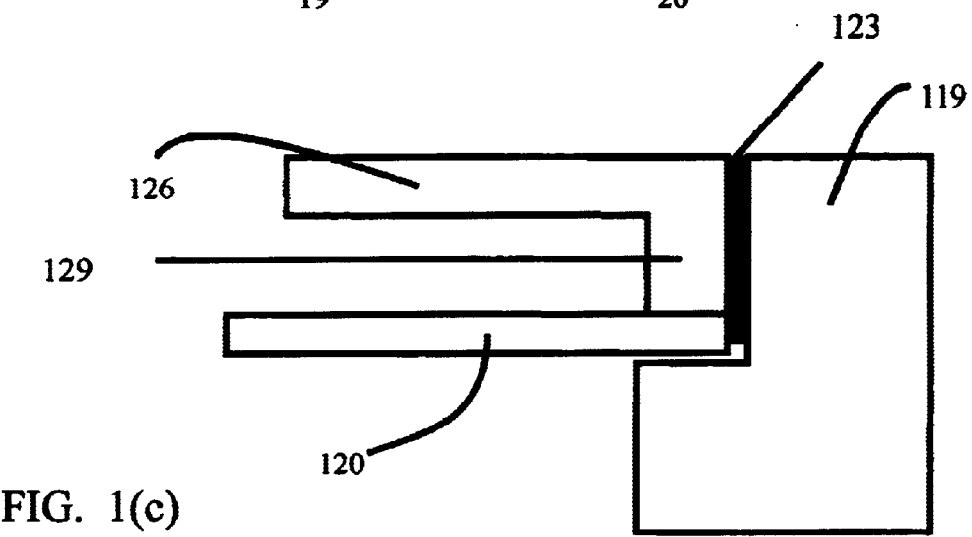
FIG. 1(c) is a sectional view of a detail of an alternative embodiment of FIG. 1(a) detailing the attachment of the synthetic muscle diaphragm within the pump housing.
Figure 2:
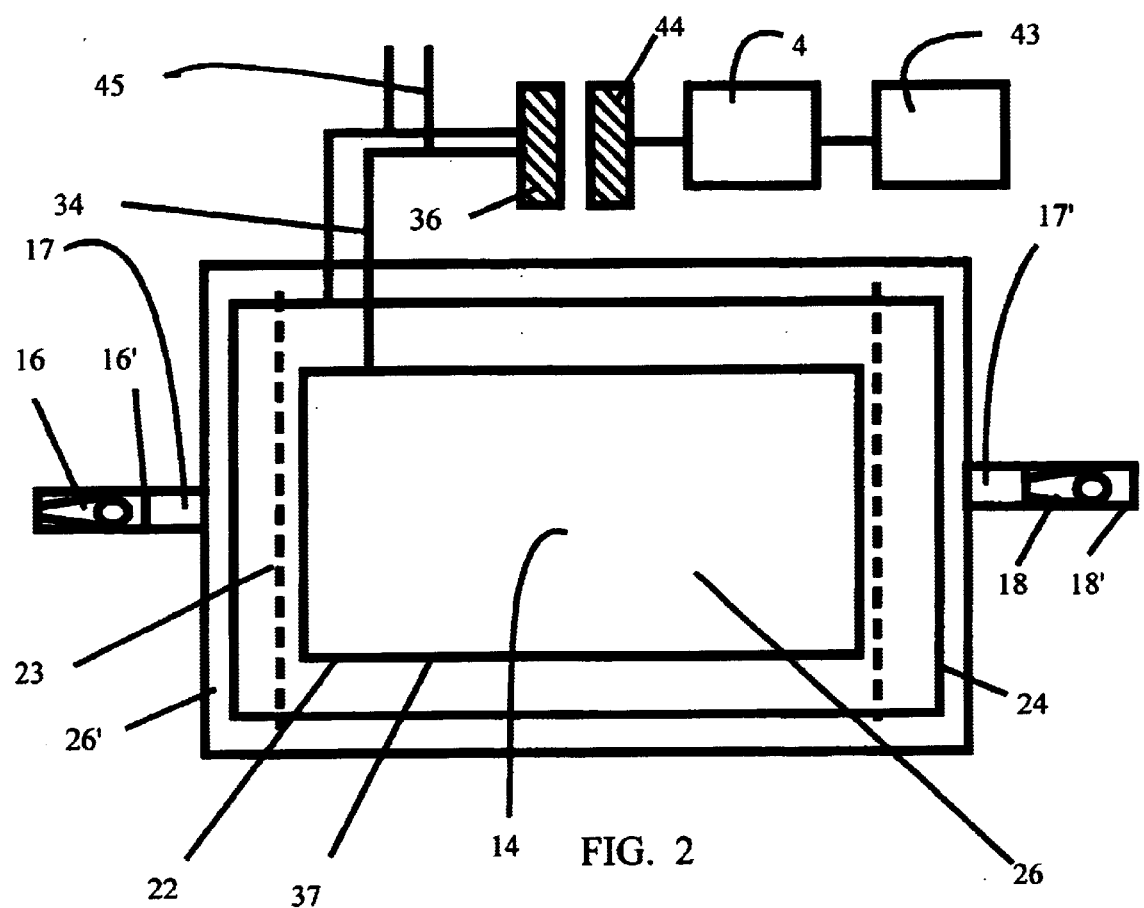
FIG. 2 is a plan view, partly in section, of the pump assembly of the present invention.

The diaphragm 20 is secured within end panels 19, 19' by top panel 26 which has its opposing end portions 26' secured within mutually opposed recesses 23 formed in the end panels 19, 19' as is shown in greater detail in FIG. 1b. Alternatively, a diaphragm 120 may be secured by mutually opposed recesses 123 formed in end panel 119 as shown in FIG. 1(c). The top panel 126 has a downwardly extending flange 129 which secures the top side of the diaphragm 120, with the horizontal surface of the recess securing the diaphragm on the underside. The top panel 26 may be sized for frictional engagement or "snap" fit within the recess 23 providing a tight seal along the entire length of the opposing end portions of the diaphragm 20 to ensure proper pumping function. Of course, an adhesive may be used to seal the top 26 within the housing 11, the adhesive serving to strengthen the connection of the diaphragm 20 within the recess. The side portions or longitudinal edges 37 of the diaphragm 20 are not secured within the housing 11 so as to allow for flexing of the synthetic muscle diaphragm 20 as will be explained in more detail later.

Electrical power is applied to the diaphragm 20 by conductors 34 electrically connected to ring electrodes 22 and 24. Ring electrode 22 is disposed on the top surface of the diaphragm 20 while ring electrode 24 is disposed on the bottom surface of the diaphragm 20. The electrodes 22, 24 may be deposited on the diaphragm 20 by electro-deposition techniques as are well known in the art. Conductors 34 may be enamel covered gold or copper wire conductors.

Figure 3:
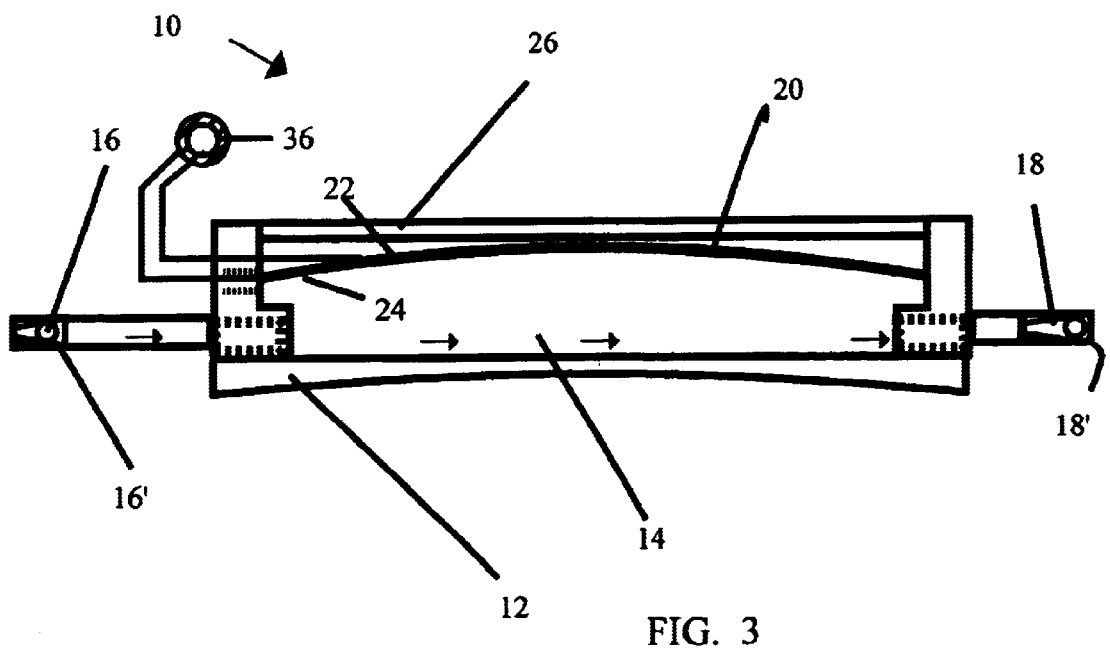
FIG. 3 is a side elevational view, partly in section, of the pump assembly of the present invention showing upward deflection of the pump diaphragm actuator.
Figure 4:
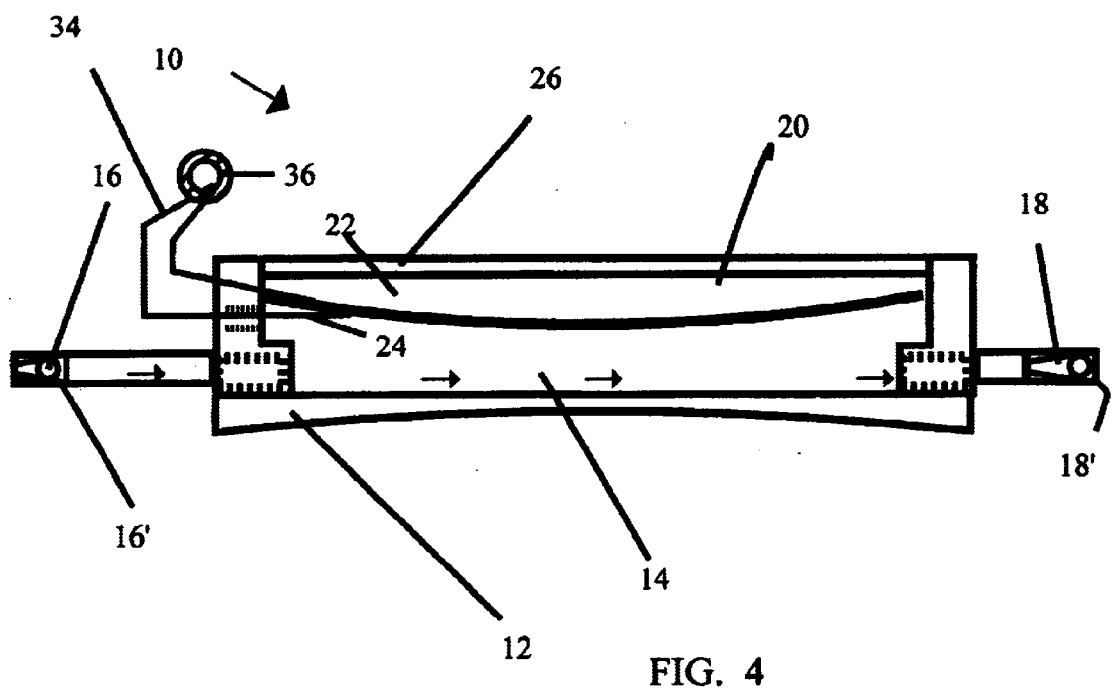
FIG. 4 is a side elevational view, partly in section of the pump assembly of the present invention showing downward deflection of the pump diaphragm actuator.

Operation of the assembly 10 may be described generally as follows. When an electrical pulse or voltage signal is applied to electrode 22 the diaphragm 20 is flexed upward as shown in FIG. 3. This causes the surrounding fluid or air to be drawn into conduit 17 forcing check valve 16 open and allowing the surrounding fluid or air to enter the pumping chamber 14. One way check valve 18 is forced closed as it allows only outward flow in conduit 17'. The pumping chamber 14 may have medicine in powder or liquid form stored therein. Pulsing electrode 24 forces the contents of pumping chamber 14 out through conduit 17' when the diaphragm 20 is flexed downward as shown in FIG. 4. Outward fluid flow via conduit 17 is prevented by one way check valve 16. Thus, a cycle of pump operation comprises upward flexure of the diaphragm 20 causing an inflow of the surrounding fluid, followed by a downward flexure of the diaphragm causing fluid to be discharged from the conduit 17'. Any medicine contained within pump chamber 14 will be mixed in with the influent due to fluid turbulence and discharged during the downward or second half of the pump cycle. Metering of the medicine may be accomplished by applying a predetermined number of electrical pulses to electrodes 22, 24 to produce a corresponding number of cycles of pump operation. The number of cycles required to deliver the desired dose can be determined by experimentation and would depend on many factors such as whether the medicine is in liquid or powder form, the solubility of the medicine in the surrounding bodily fluid, the location in the body the pump 10 is positioned, etc. It should be noted that if the assembly 10 is used to deliver drugs, it may advantageously be positioned outside the body to allow for easy refill. In this case, conduits 17, 17' may be in fluid communication with, e.g., a lumen or other means for introducing drugs either intravenously or to a predetermined treatment area.

The voltage or signal applied to electrodes 22, 24 may be provided by an induction coil 36, which, in the event the pump 10 is used as a bio-implant, may be transcutaneously powered by an induction generator or coil 44. A low power alternating voltage may be induced in the coil 36 by adjacent coil 44 which is connected to a suitable low power alternating voltage source 47. A computer or dedicated microprocessor device 43, having a power supply, and a signal generating and processing means operably connected thereto, can receive electrical signals from, as well as send electrical signals to the pump assembly 10 via voltage source 47 and coils 44 and 36. In accordance with one aspect of the invention, pump housing 11 and coil 36 may be subcutaneously implanted so that coil 36 can receive pulses from coil 44. Alternatively, coil 36 may be positioned in the pump housing 11, with the housing 11 positioned as close as possible to coil 44 to ensure inductive coupling. When coil 36 is pulsed by electromagnetic fields from coil 44, electrical signals are sent to electrodes 22, 24. The pulsing coil 44 can also receive electromagnetic fields generated by coil 36, the resulting signal may be sent to computer 43 for analysis. Thus, the pump 10 may be interrogated and its pumping action controlled in response to sensed conditions. For example, if coil 36 is fed a low voltage alternating signal via coil 44 by way of mutual induction, a computer 43 may control the signal fed to the coil 36, while monitoring the voltage/current in conductors 34 which are electrically connected to electrodes 22, 24. It should be noted that the current in conductors 34 will never be a DC current as the current will be due to either the pulsing of coil 36, random motion of the diaphragm 14, or motion associated with a much larger piece of synthetic muscle (not shown) which may be connected to leads 45, as will be explained in more detail later. In the event the pump 10 is powered solely by way of a larger piece of artificial muscle, coil 44 may be used solely for sensing the current pulses received by electrodes 22, 24. In this case, the computer 43 may be used to monitor the frequency and magnitude of the current in coil 36. A display means 49 such as a CRT may be used to display the sensed current. The display 49 may show all sensed operational parameters associated with pump 10. The display 49 may also show a control panel which may be accessed by a mouse (not shown) allowing the operator to selectively control various operational parameters such as the frequency and magnitude of voltage source 47, the display format, or resolution for displaying the sensed parameters. Alternatively, the computer 43 may be set up to selectively gate pulses to electrodes 22, 24 regardless of the type of voltage source. For example, if the current provided by a large piece of artificial muscle connected to leads 45 is too high in frequency producing rapid undulations in diaphragm 14, the computer 43 may block every other pulse to reduce the frequency by a factor of 50%. As would be apparent to one of skill in the art, the computer 43 may be a microprocessor small enough for attachment to a human body via, e.g., surgical tape, with sensing/pulsing coil 44 mounted internally to the microprocessor 43 or immediately adjacent thereto in order to send/receive voltage signals to/from coil 36.

In lieu of having an induction coil 36 coupled to an external electromagnetic field or voltage source, a synthetic muscle (not shown) may be used to generate operating voltage for the pump assembly 10. The synthetic muscle, which would be relatively large compared to the diaphragm 20, would have ring conductors attached thereto, and would be electrically connected to conductors 34 via leads 45 as has been previously described. Of course, the synthetic muscle would have to be connected to an adjacent source of mechanical energy such as a muscle when used as a bio implant. As discussed above, a computer or microprocessor 43 may be used to selectively apply voltage signals generated by the synthetic muscle to electrodes 22, 24, so as to prevent random actuation of the diaphragm 20. Flexing of the synthetic muscle by the adjacent muscle would cause current pulses in the synthetic muscle ring conductors which in turn would send current pulses to leads 45 and electrodes 22, 24.

Of course, electrical pulses may be supplied directly to electrodes 22, 24 from an alternating voltage source via leads 45.

It is to be understood that the provided illustrative examples are by no means exhaustive of the many possible uses for our invention.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims:

What is claimed is:

1. A pump assembly comprising:
   a main body having an anterior end, a posterior end, and an interior chamber;
   an intake conduit, said intake conduit fluidly coupled to said anterior end and an outlet conduit fluidly coupled to said interior chamber;
   a first valve means for selectively allowing fluid flow from said intake conduit to said interior chamber, a second valve means for selectively allowing fluid flow from said interior chamber into and through said outlet conduit;
   fluid displacement means for causing fluid flow through said main body, said fluid displacement means having a flexible main body and extending across said interior chamber;
   said fluid displacement means comprising a first synthetic muscle responsive to electrical impulses to produce movement thereof; and,
   a second synthetic muscle electrically connected to said first synthetic muscle for supplying said electrical impulses.

2. The assembly of claim 1 wherein said main body is elongated and substantially planar, and wherein one or more outer surfaces of said main body are contoured in accordance with physical parameters of an implant area.

3. The assembly of claim 1 wherein said fluid displacement means is powered by a source of electrical power.

4. The assembly of claim 1 wherein ring electrodes are disposed on opposite sides of said fluid displacement means, said ring electrodes electrically connected to said source of electrical power.

5. The assembly of claim 1 wherein said source of electrical power is a mutually inducting coil.

6. A bio-implantable pump assembly for delivering medicine comprising:
   a substantially planar main body having an anterior end, a posterior end, and an interior chamber;
   an intake conduit, said intake conduit fluidly coupled to said anterior end and an outlet conduit fluidly coupled to said interior chamber;
   a first valve means for selectively allowing fluid flow from said intake conduit to said interior chamber, a second valve means for selectively allowing fluid flow from said interior chamber into and through said outlet conduit;
   a fluid displacement means for causing fluid flow through said main body, said fluid displacement means having a flexible main body and extending across said interior chamber;
   a source of electrical power for generating electrical pulses, said source of electrical power electrically connected to electrodes disposed on opposing sides of said synthetic muscle fluid displacement means;
   a predetermined quantity of medicine stored in said interior chamber and wherein fluid flow through said interior chamber causes mixing of said medicine with the ambient fluid, a portion of said medicine dispensed through said outlet conduit with each cycle of operation of said fluid displacement means.

7. The assembly of claim 6 wherein said source of electrical power is a subcutaneously implanted inductively coupled coil.

8. The assembly of claim 7 including sensing means for sensing pulses in said inductively coupled coil, and micro processing means electrically connected to said coil for acquiring and processing said pulses.

9. The assembly of claim 8 wherein said sensing means is an adjacent coil, and said micro processing means controllably gates electrical pulses to said adjacent coil.

10. The assembly of claim 6 wherein said source of electrical power is a synthetic muscle.

* * * * *